United States Patent [19]

Hengstberger et al.

[11] Patent Number: 4,633,865
[45] Date of Patent: Jan. 6, 1987

[54] DEVICE FOR PERFORMING EXAMINATIONS AND INTERVENTIONS IN THE ABDOMINAL CAVITY OF A PATIENT

[75] Inventors: Maria Hengstberger; Herbert Hengstberger, both of Vienna, Austria; Harry Mönch, Knittlingen, Fed. Rep. of Germany

[73] Assignee: Rewoplan medizin-technische Einrichtungsgesellschaft mbH, Fed. Rep. of Germany

[21] Appl. No.: 632,299

[22] Filed: Jul. 19, 1984

[51] Int. Cl.$^4$ .............................................. A61B 17/00
[52] U.S. Cl. ...................................... 128/303 R; 128/3
[58] Field of Search ................... 128/303 R, 361, 3; 604/115, 176, 313–316, 346

[56] References Cited

U.S. PATENT DOCUMENTS

| | | | |
|---|---|---|---|
| 2,917,050 | 12/1959 | Kenyon | 128/361 |
| 3,122,138 | 2/1964 | Geary | 604/115 |
| 3,815,598 | 6/1974 | Vass et al. | 604/176 |
| 3,896,810 | 7/1975 | Akiyama | 604/176 X |

FOREIGN PATENT DOCUMENTS

| | | | |
|---|---|---|---|
| 31254 | 2/1904 | Switzerland | 604/313 |
| 2995 | of 1911 | United Kingdom | 604/346 |
| 1048558 | 11/1966 | United Kingdom | 604/313 |
| 1180932 | 2/1970 | United Kingdom | 128/361 |

Primary Examiner—Michael H. Thaler
Attorney, Agent, or Firm—Hill, Van Santen, Steadman & Simpson

[57] ABSTRACT

A device for use in performing examinations and surgical interventions within the abdominal cavity of a patient comprises a cowling having a marginal area which is applicable to the abdominal integument of the patient and which is provided with an upper temporarily closable opening in communication with an annular projection which is directed into the inside of the cowling and which has a free end which is applicable in hermetic contact with the abdominal integument, whereby a negative pressure generated within the cowling raises the abdominal integument. Optional instruments may thereupon be inserted through the opening and via the abdominal integument into the abdominal cavity without damaging any internal organs and vessels which were initially in contact with the inner side of the abdominal integument.

6 Claims, 5 Drawing Figures

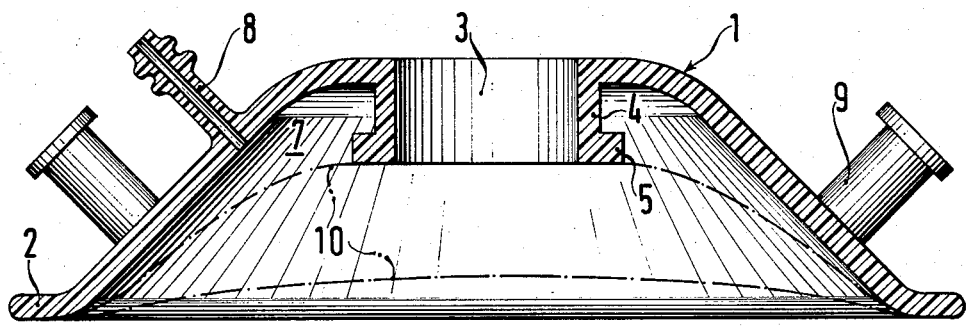
FIG. 1
FIG. 2
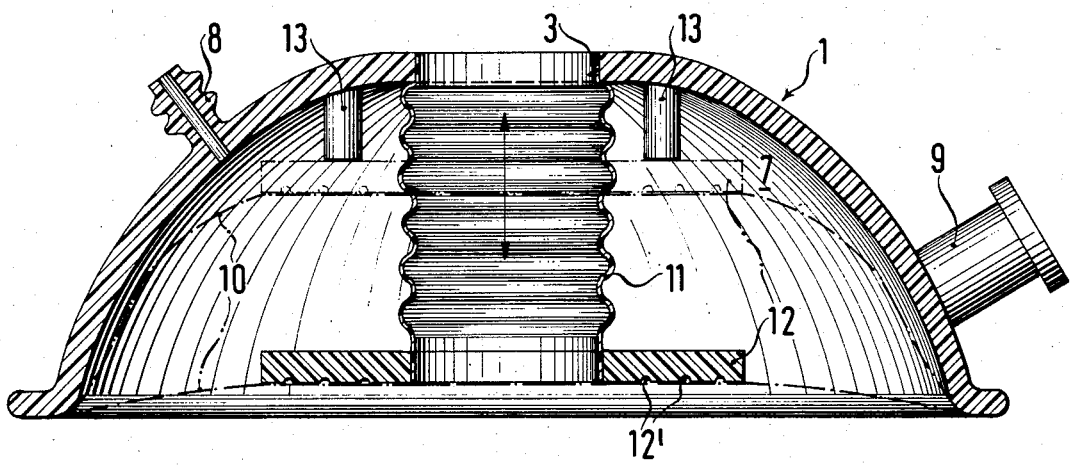

DEVICE FOR PERFORMING EXAMINATIONS AND INTERVENTIONS IN THE ABDOMINAL CAVITY OF A PATIENT

BACKGROUND OF THE INVENTION

1. Field of the Invention

This invention relates to a device for performing examinations by means of laparoscopes and for performing surgical interventions within the abdominal cavity of patients.

2. Description of the Prior Art

Abdominal integuments have to be transpierced for examination of the abdominal cavities of patients by means of laparoscopes and for the performing of surgical interventions in the abdominal cavity, for the insertion of a cannula, by means of which the abdominal cavity may be filled with an inert gas and the abdominal integument may be raised, so that instruments may be inserted through the abdominal integument without danger to the internal organs. The perforation of the abdominal integument raises the risk of injuring internal organs, in particular intestinal loops and vessels, lying in contact with the inner side of the abdominal integument. Other disadvantages of the known method consist in that it is of time-consuming nature, since say 4 to 6 liters of gas must be blown into the abdominal cavity to raise the abdominal integument, which requires a period of at least ten minutes. Although this gas is released again or emerges from the abdominal cavity through the aperture present in the abdominal integument after completion of the examination or operation, gaseous residues are left behind in said abdominal cavity, which afflict the patient with difficulties for a period of several days. Finally, the known method is also disadvantageous and onerous in its application, inasmuch as it requires covering the parts of the body around the location where the abdominal integument is perforated, so that sterile conditions during interventions are assured.

SUMMARY OF THE INVENTION

The main object of the present invention is to provide a device whereby the abdominal integument may be lifted off the internal organs without application of a pneumoperitoneum, and which is intended to allow of transpiercing the abdominal integument in its raised position, so that instruments may subsequently be inserted and examinations and interventions may be performed within the abdominal cavity.

To this end, the present invention consists in a device for use in performing examinations and interventions within an abdominal cavity of a patient, said device being characterized by a cowling having a marginal area which is adapted to be placed in contact with the abdominal integument, means defining a temporarily closable opening in an upper portion of the cowling, and an annular projection directed into the inside of the cowling, said annular projection having a free end which is applicable in hermetic contact with the abdominal integument, whereby the abdominal integument may be raised by generating a negative pressure within the cowling.

By means of the invention, the abdominal integument may be lifted off the internal organs and vessels by means of the negative pressure within the cowling, so that the abdominal integument may be transpierced subsequently via the opening in the cowling and instruments may be inserted through the same opening into the abdominal cavity for examinations and surgical interventions. In the case of a complementarily required application of a pneumoperitoneum, it is assured that a cannula may be pushed through the raised abdominal integument without injury to internal organs and vessels.

Advantageously, the opening in the cowling is centrally disposed.

In one embodiment of the invention, the annular projection constitutes an extension of the periphery of said opening and is in the form of a tubular stub.

Preferably, the opening in the cowling is closed off, after being placed on the abdominal integument, with a hand or by means of a hermetically applicable and removable cover, until the abdominal integument is caused to establish a hermetic seal between the internal volume of the cowling and the atmosphere by contact with the annular projection, by means of the negative pressure applied. The hand or cover may be lifted off subsequently, so that instruments may be inserted without obstruction so far as the abdominal integument and into the abdominal cavity.

Instead of utilising a closure for the opening, the annular projection may be formed as a bellows which at its free end is provided with an annular plate for placing in contact with the abdominal integument and the internal volume of the cowling between the bellows and the cowling wall is connected to a vacuum pipe via a connector.

BRIEF DESCRIPTION OF THE DRAWINGS

In order that the invention may be more readily understood, some embodiments thereof will now be described, by way of example, with reference to the accompanying drawings, in which:

FIG. 1 is a vertical median cross-sectional view through a cowling of one embodiment of a device, which is constructed according to the invention, for use in performing examinations and surgical interventions within the abdominal cavity of a patient, FIG. 2 is a vertical cross-sectional view of a cowling of a second embodiment.

DESCRIPTION OF THE PREFERRED EMBODIMENTS

Figure 3:
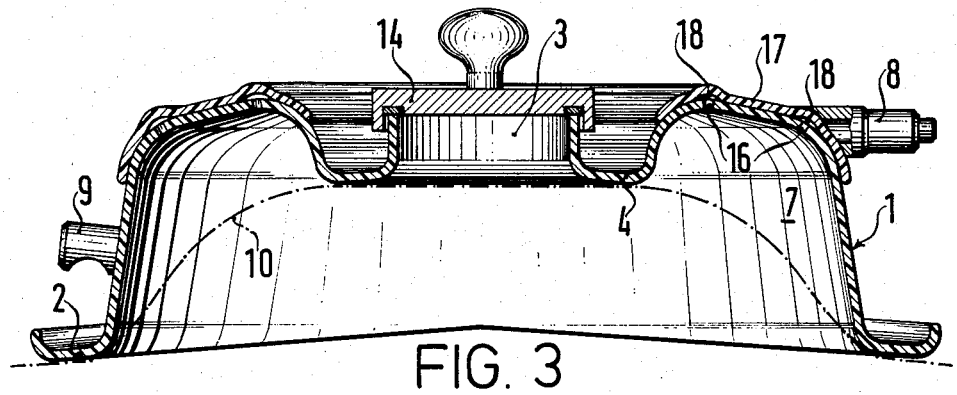
FIG. 3 is a vertical cross-sectional view of a cowling of a third embodiment taken along line III—III of FIG. 4.

Referring to FIG. 1, there is shown a cowling 1 having its free rim 2 placed on the abdominal integument 10 of a patient. The cowling 1 is provided, in its central surface section, with an opening 3 followed by an inwardly directed projection formed by tubular stub 4 having at its bottom edge a contact flange 5. A connector 8 projects from the cowling 1 for connection to a source of negative pressure, and handles 9 are provided on the cowling 1 for manipulating the same or for suspension in a securing device.

A pipe (not shown) leading to a source of negative pressure is connected to the connector 8. To establish a negative pressure within the internal volume 7 defined by the cowling 1 and the abdominal integument 10, the opening 3 is temporarily closed off hermetically, e.g. by placing a hand or lid 14 (see FIG. 3) thereon, and then a negative pressure is generated within the internal volume 7. The abdominal integument 10 is raised thereby until it comes into contact with the flange 5 of the stub 4. This position of the abdominal integument 10 is illustrated by chain lines in FIGS. 1 to 3. Since the internal volume 7 between the abdominal integument 10 and the cowling 1 is placed under vacuum, the opening 3 may be utilised for insertion of instruments for examinations and interventions.

Instead of closing off the opening 3 by hand or with the cover 14 (FIG. 3) temporarily during connection of the cowling to a source of negative pressure, it is also possible to proceed in the manner shown in FIG. 2 to which reference will now be made. In FIG. 2, a bellows projection 11 extends into the inside of the cowling 1 from the rim of the opening 3 and is provided at its lower free end with an outer annular plate 12 comprising bottom annular grooves 12a. The annular plate 12 is placed on the abdominal integument 10, and the internal volume 7 defined by the bellows 11, the cowling 1 and the abdominal integument 10 is connected to a source of negative pressure via the connector 8. Upon applying the negative pressure, the annular plate 12 is raised together with the abdominal integument under contraction of the bellows 11 until the annular plate 12 occupies the position shown by the dashed lines in which it bears tightly against internal projections 13, so that, again, instruments of the kind referred to may be brought into action via the opening 3 for examinations and interventions.

In the embodiments of FIGS. 1 and 2, the vacuum connector 8 is situated substantially in the area of the sidewall of the cowling 1. In this connection, the case may arise that the lifting abdominal integument 10 also blocks the connector stub 8, so that the negative pressure prevailing within the internal volume 7 may not be sufficient to assure uniform retention of the lifted abdominal integument throughout the free rim 2.

Figure 4:
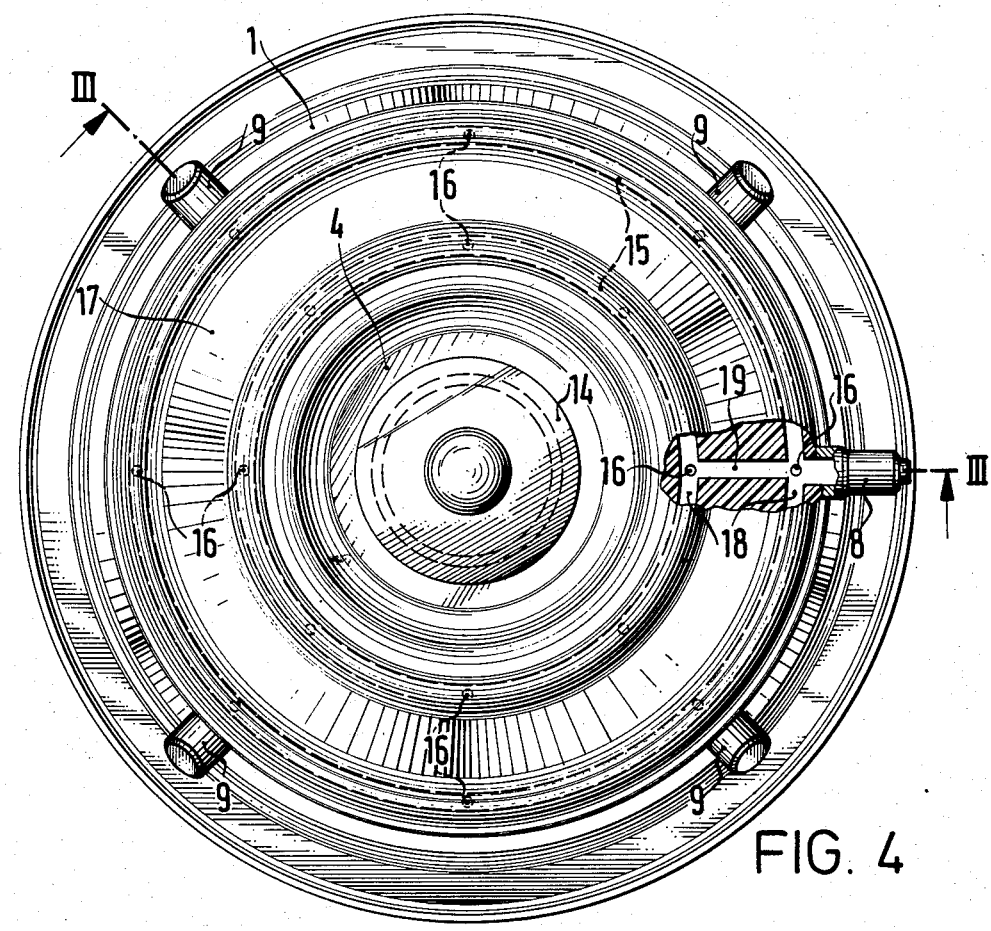
FIG. 4 is a plan view with a portion broken away for purposes of illustration of the cowling of the embodiment of FIG. 3.

To prevent this blocking of the vacuum connector 8 in any event, one or more circularly arranged lines 15 of orifices 16 are provided in the upper portion of the cowling, as shown in FIGS. 3 and 4. These orifices 16 are covered by an annular areal member 17 which in conjunction with the cowling forms two annular passages 18 which extend along the two circular lines 15 and which interconnect the orifices 16. A radial passage 19 which interconnects the annular passages 18 is complementarily formed between the areal member 17 and the cowling 1, and is followed by a connector 8 for connection to the vacuum source. The evacuation of the air thus occurs at an appreciable distance from the abdominal integument, so that blocking of the passages 16 by the lifting abdominal integument is prevented in any event, since the said integument comes into contact with the lower rim of the annular projection 4. In the embodiment of FIGS. 3 and 4, the inwardly directed projection 4 is formed as an extension of the wall of the cowling, i.e. by an annular corrugation of the cowling surface and having its peak directed into the inside of the cowling. The cowling 1 and the annular areal member 17 may advantageously be produced from a suitable plastics material which may be transparent or pigmented.

Figure 5:
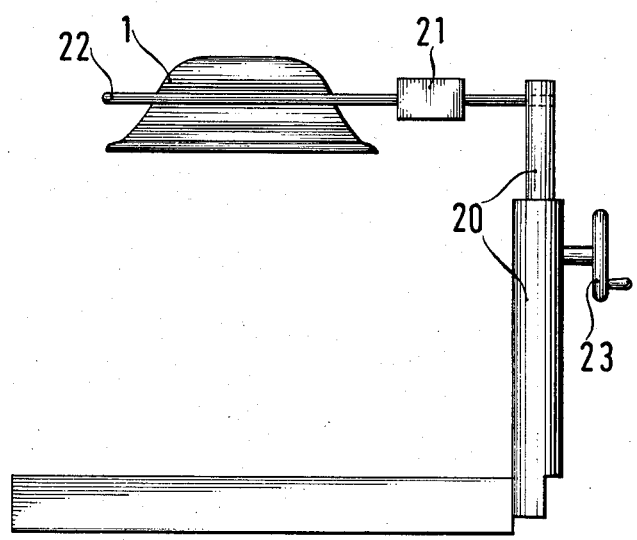
FIG. 5 is a diagrammatic side elevation of one form of support for vertical adjustment of the cowling of any one of the embodiments of FIGS. 1 to 4.

As shown in FIG. 5, the cowling 1 may advantageously be adjustable in height within a support 21, 22 by means of a crank 23, e.g. by means of a bearer 20 attached to the treatment table. After evacuation, the cowling 1 may thereby be raised for additional lifting of the abdominal integument, to obtain and secure the optimum raised position of the abdominal integument.

It should be observed in conclusion, that the area of the base may differ geometrically from a plane surface to match the lower marginal area of the cowling to the shape of the bodily surface. The annular vacuum space 7 resulting during evacuation of the cowling placed on the abdominal integument may furthermore be divided into separate vacuum compartments, e.g. by the fact that as in the embodiment of FIGS. 3 and 4, radial partitions situated in the radial plane extend from the annular projection 4 to the periphery, whereof the lower edge is adapted to the outline of the lifted abdominal surface 10.

Although particular embodiments have been described, it should be appreciated that various modifications may be made without departing from the scope of the invention.

We claim:

1. A device for use in performing examinations and surgical operations within an abdominal cavity of a patient after an abdominal integument has been pierced to allow insertion of a known instrument into the cavity, said device comprising a cowling having an interior and a marginal section for sealingly engaging the abdominal integument, said cowling having means for connecting a source of vacuum to the interior of the cowling including a connector, said cowling having means for forming a temporarily closable opening in the upper portion of said cowling with an annular projection directed into the interior of the cowling, said annular projection being an annular corrugation of the cowling surface with a U shape and a bight portion of the corrugation extending into the interior of the cowling to form a free end for creating a sealing contact with the abdominal integument, said means for connecting to a source of vacuum including first means for defining at least one circular line of orifices and second means for defining at least one connecting space for the circular orifices having a radial passage extending to said connector so that the abdominal integument may be raised by temporarily closing said opening and generating a negative pressure within the interior of the cowling and when raised the abdominal integument can be pierced by an instrument extending through said opening.

2. A device according to claim 1, wherein said first means are orifices in said cowling and said second means comprise an annular sheet member secured to said cowling to cover said orifices, said annular sheet member being embossed to form said connecting spaces and radial passages.

3. A device according to claim 2, wherein said cowling has at least two circular lines of orifices and said annular sheet member has embossments for the connecting spaces for each of said two circular lines of orifices.

4. A device according to claim 2, wherein the cowling and the annular sheet member consist of transparent plastic materials.

5. A device according to claim 2, wherein the cowling and the annular sheet member consist of a pigmented plastic member.

6. A device for use in performing examinations and surgical operations within an abdominal cavity of a patient after an abdominal integument has been pierced to allow insertion of a known instrument into the cavity, said device comprising a cowling having an interior and a marginal section for sealingly engaging the abdominal integument, said cowling having means on an outer surface for attaching the cowling to a vertical adjustable carrier, said cowling having means for connecting a source of vacuum to the interior of the cowling including a connector, said cowling having means for forming a temporarily closable opening in the upper portion of said cowling with an annular projection directed into the interior of the cowling, said annular projection having a free end for creating a sealing contact with the abdominal integument so that the abdominal integument may be raised by temporarily closing said opening and generating a negative pressure within the interior of the cowling and when raised the abdominal integument can be pierced by an instrument extending through said opening.

* * * * *